(12) United States Patent
Trombley, III et al.

(10) Patent No.: US 10,105,486 B2
(45) Date of Patent: Oct. 23, 2018

(54) FLUID PATH CONNECTORS AND CONTAINER SPIKES FOR FLUID DELIVERY

(71) Applicant: BAYER HEALTHCARE LLC, Indianola, PA (US)

(72) Inventors: Frederick W. Trombley, III, Gibsonia, PA (US); David M. Reilly, Pittsburgh, PA (US)

(73) Assignee: BAYER HEALTHCARE LLC, Whippany, NJ (US)

(*) Notice: Subject to any disclaimer, the term of this patent is extended or adjusted under 35 U.S.C. 154(b) by 24 days.

(21) Appl. No.: 15/173,962

(22) Filed: Jun. 6, 2016

(65) Prior Publication Data
US 2016/0279326 A1    Sep. 29, 2016

Related U.S. Application Data

(62) Division of application No. 13/646,886, filed on Oct. 8, 2012, now Pat. No. 9,358,333, which is a division
(Continued)

(51) Int. Cl.
*A61M 5/162* (2006.01)
*A61M 5/00* (2006.01)
(Continued)

(52) U.S. Cl.
CPC ............ *A61M 5/162* (2013.01); *A61M 5/007* (2013.01); *A61M 39/24* (2013.01); *A61J 1/1406* (2013.01);
(Continued)

(58) Field of Classification Search
CPC .............................. A61M 5/162; A61M 5/007
See application file for complete search history.

(56) References Cited

U.S. PATENT DOCUMENTS 2,757,670 A * 8/1956 Ogle ..................... A61M 5/162
604/251
3,625,858 A    12/1971 Conn
(Continued)

OTHER PUBLICATIONS

International Search Report and Written Opinion for International Application No. PCT/US2010/047126 dated Oct. 20, 2010.

*Primary Examiner* — Kevin Lee
(74) *Attorney, Agent, or Firm* — Joseph L. Kent; David Schramm; James R. Stevenson

(57) ABSTRACT

A fluid connector includes an extending section having a spiked end to pierce a container port. The extending section includes at least one air conduit and at least one fluid conduit therethrough. The extending section further includes first and second abutment members. The first abutment member is adapted to abut a first or air side of the container port upon piercing of the container port, and the second abutment member, which is spaced from the first abutment member, is adapted to abut a second or fluid side of the container port. The fluid connector can further include grasping members extending from the extending section to facilitate rotation of the extending section relative to the container port during piercing thereof. The fluid connector can also include a check valve in fluid connection with the at least one air conduit. The check valve may be positioned within the extending section.

9 Claims, 13 Drawing Sheets

Related U.S. Application Data of application No. 12/550,786, filed on Aug. 31, 2009, now Pat. No. 8,281,807.

(51) Int. Cl.
  *A61M 39/24* (2006.01)
  *B33Y 70/00* (2015.01)
  *B33Y 80/00* (2015.01)
  *A61J 1/14* (2006.01)

(52) U.S. Cl.
  CPC ...... *A61M 2005/1623* (2013.01); *B33Y 70/00* (2014.12); *B33Y 80/00* (2014.12); *Y10T 137/3115* (2015.04); *Y10T 137/7856* (2015.04); *Y10T 137/8122* (2015.04); *Y10T 137/86348* (2015.04)

(56) References Cited

U.S. PATENT DOCUMENTS

| | | |
|---|---|---|
| 3,857,909 A | 12/1974 | Huggins |
| 3,880,179 A | 4/1975 | Lenz et al. |
| 4,201,208 A | 5/1980 | Cambio, Jr. |
| 4,341,078 A | 7/1982 | Weitzen |
| 4,898,209 A | 2/1990 | Zbed |
| 5,290,254 A | 3/1994 | Vaillancourt |
| 5,569,181 A | 10/1996 | Heilman et al. |
| 5,685,866 A | 11/1997 | Lopez |
| 5,806,519 A | 9/1998 | Evans, III et al. |
| 5,817,082 A | 10/1998 | Niedospial, Jr. et al. |
| 5,843,037 A | 12/1998 | Uber, III |
| 5,885,216 A | 3/1999 | Evans, III et al. |
| 5,895,383 A | 4/1999 | Niedospial, Jr. |
| 5,902,298 A | 5/1999 | Niedospial, Jr. et al. |
| 5,916,197 A | 6/1999 | Reilly et al. |
| 6,071,270 A | 6/2000 | Fowles et al. |
| 6,197,000 B1 | 3/2001 | Reilly et al. |
| 6,378,576 B2 | 4/2002 | Thibault et al. |
| 6,394,992 B1 | 5/2002 | Sjoeholm |
| 6,485,479 B1 | 11/2002 | Knierbein |
| 6,499,617 B1 | 12/2002 | Niedospial, Jr. et al. |
| 6,599,273 B1 | 7/2003 | Lopez |
| 6,651,956 B2 | 11/2003 | Miller |
| 7,297,140 B2 | 11/2007 | Orlu et al. |
| 7,597,220 B2 | 10/2009 | Lim |
| 7,744,584 B2 | 6/2010 | Seward et al. |
| 7,845,522 B2 | 12/2010 | Grill |
| 8,336,577 B2 | 12/2012 | MacNeal et al. |
| 8,348,903 B2 | 1/2013 | Baplue et al. |
| 8,523,838 B2 | 9/2013 | Tornqvist |
| 2001/0000793 A1 | 5/2001 | Daubert et al. |
| 2005/0070853 A1 | 3/2005 | Gatton et al. |
| 2007/0016161 A1 | 1/2007 | Costa et al. |
| 2011/0004143 A1 | 1/2011 | Beiriger et al. |
| 2011/0295209 A1* | 12/2011 | Fangrow, Jr. ......... A61M 5/158 604/180 |
| 2012/0022399 A1 | 1/2012 | Mumaw |
| 2017/0333640 A1* | 11/2017 | Sharma ............ A61M 5/31596 |

* cited by examiner

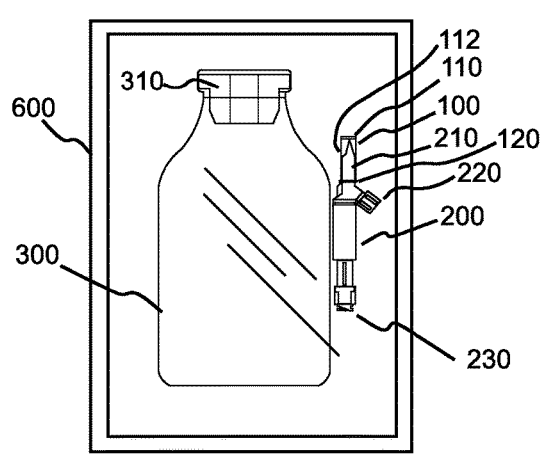
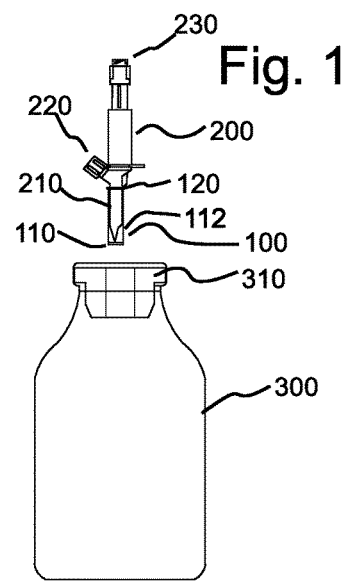
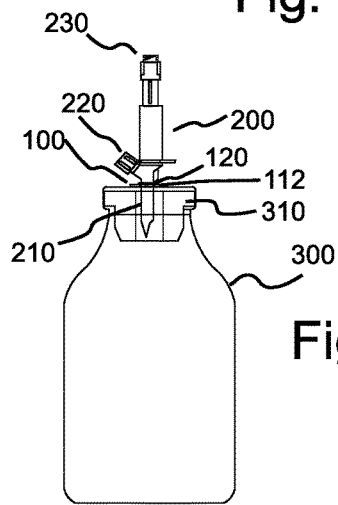
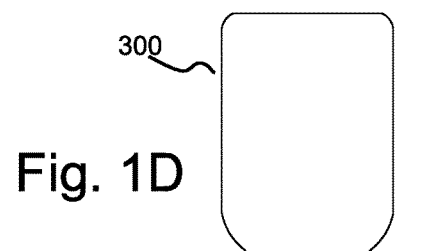
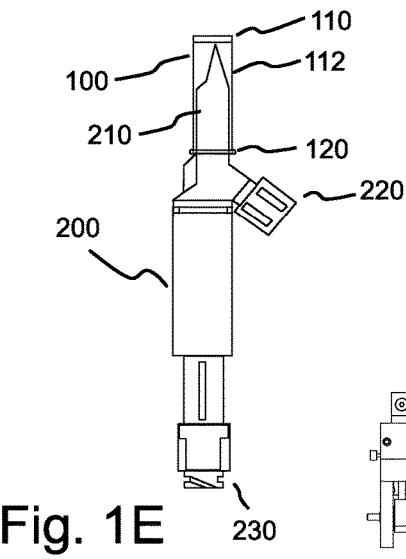
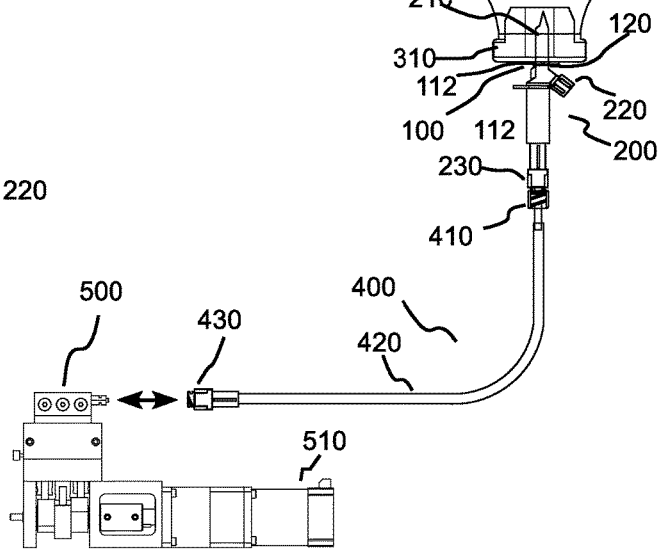

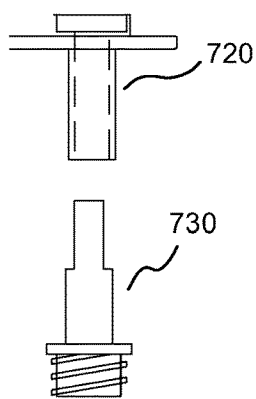
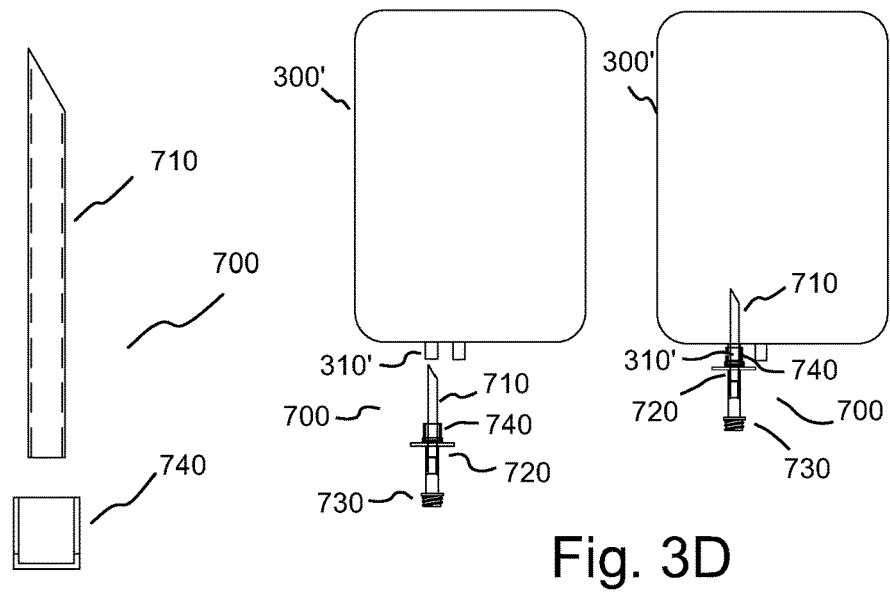
Fig. 3D
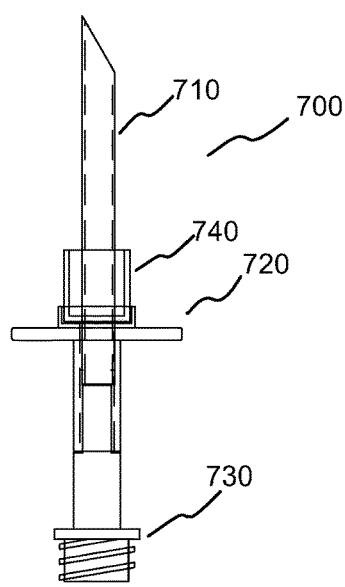
Fig. 3A
Fig. 3B
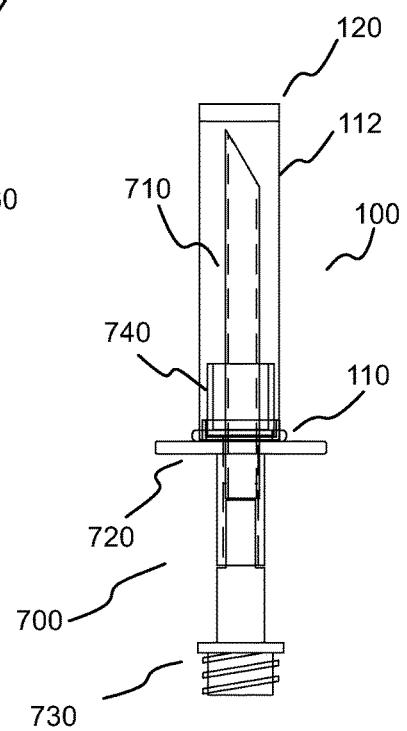
Fig. 3C

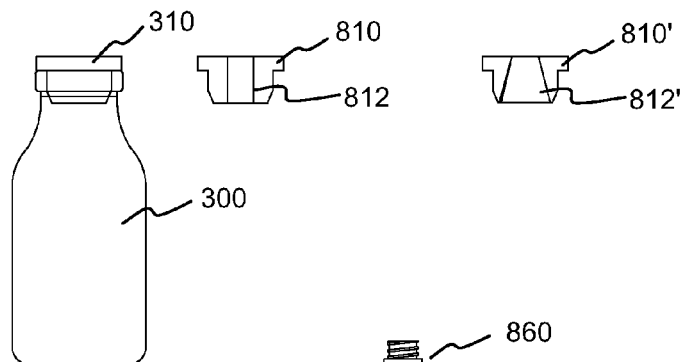
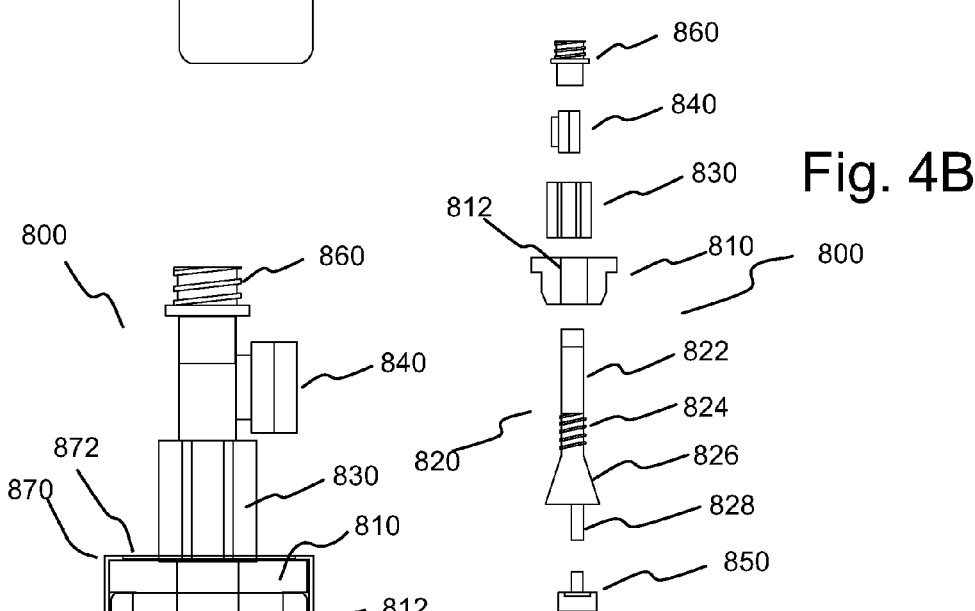
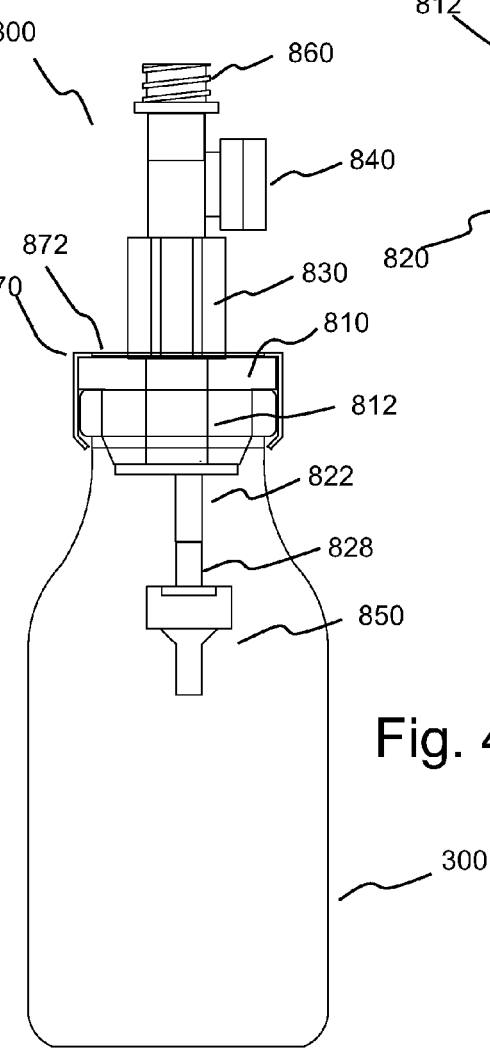
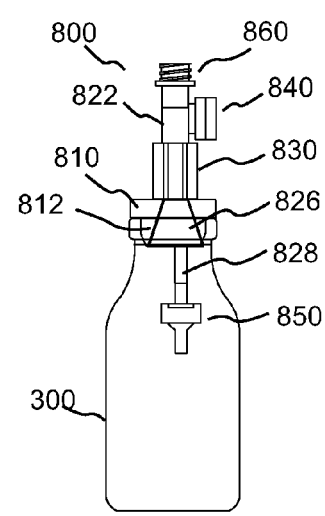
Fig. 4A
Fig. 4B
Fig. 4C
Fig. 4D

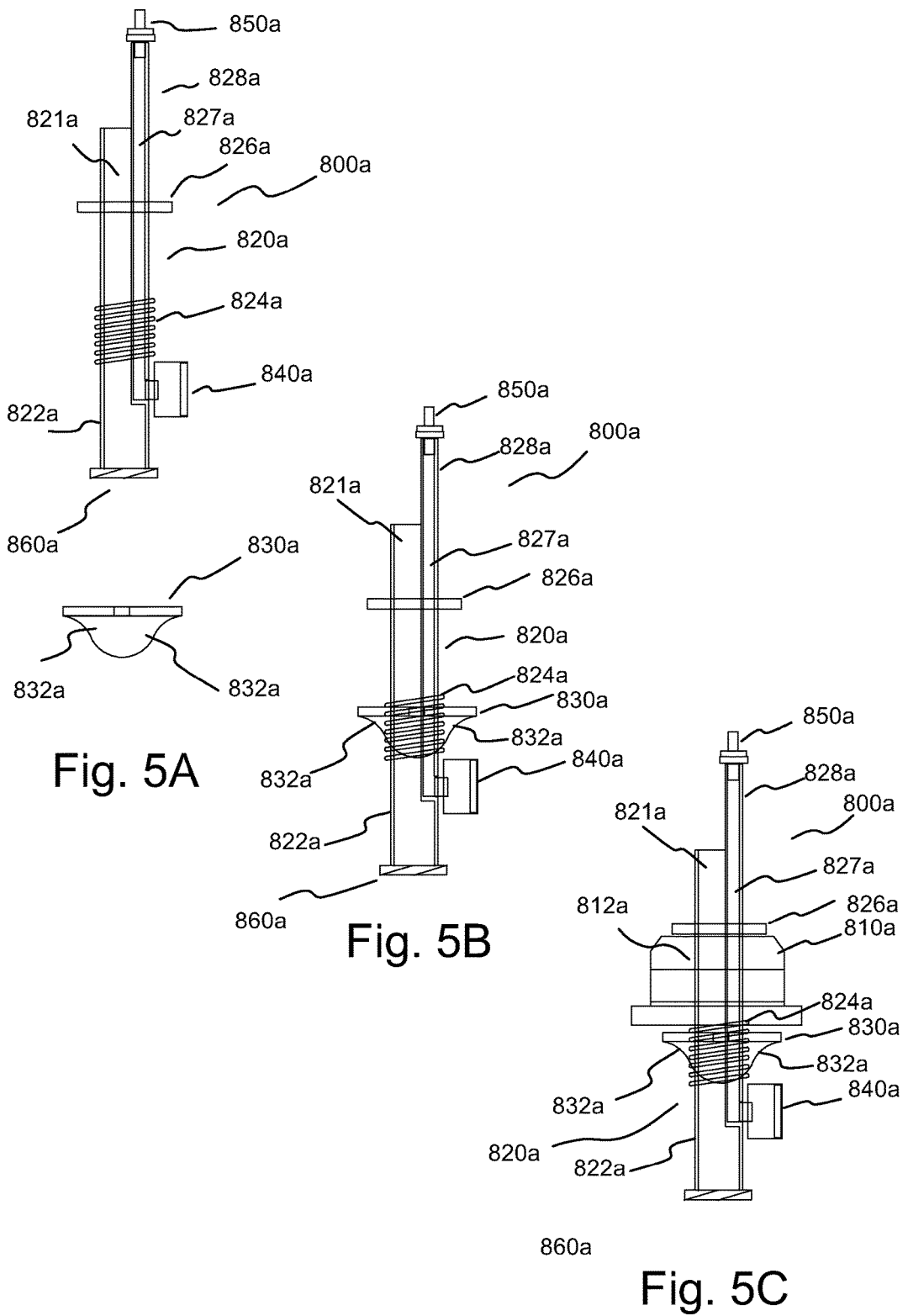

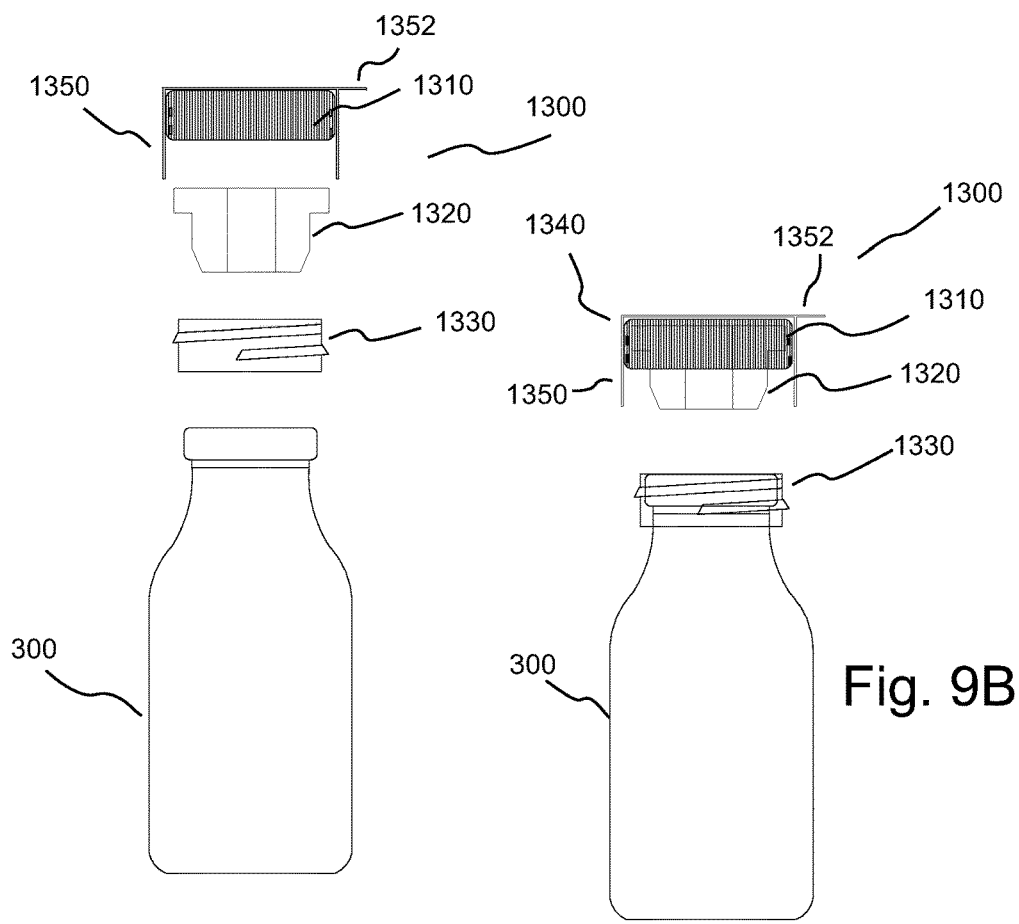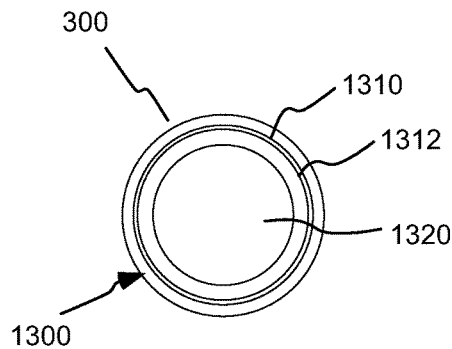

FLUID PATH CONNECTORS AND CONTAINER SPIKES FOR FLUID DELIVERY

CROSS REFERENCE TO RELATED APPLICATION

This application is a Divisional application of U.S. application Ser. No. 13/646,886, filed Oct. 8, 2012, now U.S. Pat. No. 9,358,333 which claims priority to and benefit of U.S. patent application Ser. No. 12/550,786, filed Aug. 31, 2009, now U.S. Pat. No. 8,281,807, the disclosures of which are incorporated herein by reference in their entirety.

BACKGROUND

The present invention relates to fluid path connectors and container spikes for fluid delivery and, particularly, to fluid path connectors and container spikes for delivery of sterile, medical fluids.

The following information is provided to assist the reader to understand the invention disclosed below and the environment in which it will typically be used. The terms used herein and objectives described herein are not intended to be limited to any particular narrow interpretation unless clearly stated otherwise in this document. References set forth herein may facilitate understanding of the present invention or the background of the present invention. The disclosure of all references cited herein are incorporated by reference.

In many medical procedures, such as diagnostic and/or therapeutic drug delivery, it is desirable to inject a fluid into a patient. For example, numerous types of contrast media (often referred to simply as contrast) are injected into a patient for many diagnostic and therapeutic imaging procedures. In some medical procedures (for example, computed tomography (CT), angiography, and nuclear magnetic resonance/magnetic resonance imaging (MRI)) it is desirable to deliver a liquid such as contrast medium in a timed fashion under relatively high pressures. Such relatively high pressures and timed boluses are typically achieved through the use of powered injectors.

To, for example, optimize contrast volume delivery, minimize waste of contrast and facilitate injector procedures for operators, fluid delivery systems that are capable of delivering sufficient contrast for multiple injection procedures from a single source of contrast have recently been developed. Examples of such systems are described generally in U.S. Pat. Nos. 5,569,181, 5,806,519, 5,843,037 and 5,885,216, the disclosures of which are incorporated herein by reference. Typically, it is desirable that such fluid delivery systems include a fluid path with a disposable patient interface that is changed/discarded between each patient to reduce the potential for cross-contamination.

A fluid path connector to connect to a source of fluid is required to incorporate a removable/disposable patient interface in the fluid path of a fluid delivery or injector system. However, many fluid path connectors used in medical procedures exhibit a number of substantial drawbacks including, for example, difficulty of use and difficulty in maintaining sterility. Moreover, when such connectors are used at high pressures, leakage and failure also become substantial problems.

Often a piercing member of spike is used to form a fluid connection with a fluid source or container via puncturing of an elastomeric septum or stopper on an outlet of the container. In addition to problems associated with, for example, difficulty of use and difficulty in maintaining sterility, it is often difficult to provide a suitable flow rate for certain medical procedures (for example, delivery of a relatively viscous fluid such as a contrast medium) from spike connectors. The spike of such fluid connectors is typically of limited cross-sectional area to facilitate piercing, resulting in significant limits upon the size of the fluid line or channel passing through the spike. For example, even the largest fluid line in currently available spike fluid connectors have a cross-sectional area of approximately 0.08 in$^2$, significantly limiting the flow rate of fluids therethrough.

It is desirable to develop improved fluid path connectors for fluid delivery that, for example, reduce or eliminate the above and/or other problems associated with currently available fluid path connector and spikes.

BRIEF SUMMARY

In one aspect, a fluid connector for use with a pierceable container port is provided. The fluid connector includes an extending section including a spiked end to pierce the container port. The extending section includes at least one air conduit and at least one fluid conduit therethrough. The extending section further includes a first abutment member and second abutment member. The first abutment member is adapted to abut a first or air side of the container port upon piercing of the container port. The second abutment member is spaced from the first abutment member and is adapted to abut a second or fluid side of the container port. The fluid connector can further include grasping members extending from the extending section to facilitate rotation (including twisting) of the extending section relative to the container port during piercing thereof. The fluid connector can also include a check valve in fluid connection with the air line. In several embodiments, the check valve is positioned within the extending section.

In another aspect, a fluid connector system includes a stopper including a first or air side, a second or fluid side and a passage therethrough from the first side to the second side. The fluid connector system further includes a connector including a base having at least one air conduit and at least one fluid conduit therethrough. The base further includes an extending section adapted to extend through the passage. The extending section includes a first abutment member adapted to abut the first side of the stopper and a second abutment member spaced from the first abutment member and adapted to abut the second side of the stopper and seal the passage.

In several embodiments, the first abutment member is operatively connectible to the base to maintain the second abutment member in compressive contact with the stopper. The first abutment member can, for example, include threading which cooperates with threading on the extending section of the base.

The second abutment member can, for example, include a wedge-shaped section, at least a portion of which enters the passage of the stopper. The second abutment member can alternatively include a radially outward extending flange to abut and apply compressive force to the second side of the stopper.

The fluid connector system can further include a filter in fluid connection with the air line. The fluid connector can also include a check valve in fluid connection with the air conduit on an end of the air conduit interior to the container.

The extending section can also include a cooperating connector adapted to place a fluid path element in fluid connection with the base. The cooperating connector can, for example, include a luer connector.

In several embodiments, at least a portion of the connector is sealed within the container. The connector can further include a pull tab section attached to an end of the extending section of the base and extending from the first side of the stopper to enable a user to pull the extending section of the base through the passage in the stopper so that the second abutment member abuts the stopper. In several embodiments, the first abutment member extends radially outward from the extending section of the base and is spaced from the second abutment member so that upon pulling a length of the extending section through the passage, the first abutment member contacts the first side of the stopper and maintains the second abutment member in compressive and sealing abutment with the stopper. The pull tab section can be removably attached to the extending section via a cooperating connector on the extending section. The cooperating connector can be adapted to place a fluid path element in fluid connection with the base. The cooperating connector can, for example, include a luer connector.

In another aspect, a system to connect to an outlet of a container includes a cap assembly including an annular cap member connected to a pierceable stopper. The cap member includes an opening to provide access to the pierceable stopper and a connector section removably connectible to the container. The system can further include a connector member attachable to the outlet of the container. The connector member includes a cooperating connector section to which the connector section of the cap assembly is removably attachable. The connector section can, for example, include threading, and the cooperating connector section can include cooperating threading. The connector and the cap assembly can, for example, form a removably sealed attachment to seal the outlet of the container.

In another aspect, a fluid connector includes a spike to pierce a pierceable section of a container and a flexible cover encompassing at least a portion of the spike. The flexible cover is penetrated by the spike when force is applied to the spike to pierce the pierceable section of the container.

In several embodiments, the spike includes a fluid line having a minimum cross-sectional area of at least 0.02 in$^2$.

The flexible cover can, for example, be formed from a generally cylindrical layer or film of polymeric material which is sealed on an end thereof.

In several embodiments, the flexible cover includes a generally annular elastomeric member to maintain the flexible cover in encompassing connection with the spike.

In another aspect, a fluid delivery system includes a fluid bag including at least one pierceable port and a fluid connector including a spike. A fluid line in the spike has a minimum cross-sectional area of at least 0.02 in$^2$.

In another aspect, a fluid delivery system includes a fluid connector including a fluid line and a vent line therethrough. A source of pressurized gas is in fluid connection with the vent line.

In a further aspect, a method of connecting a fluid connector to a pierceable container port, includes piercing the container port with an extending section including a spiked end. The extending section includes at least one air conduit and at least one fluid conduit therethrough. The extending section also includes a first abutment member and second abutment member spaced from the first abutment member. The method further includes extending the extending section through the container port so that the first abutment member abuts a first or air side of the container port and the second abutment member abuts a second or fluid sided of the container port.

In another aspect, a method of forming a fluid connection with a container, which includes an outlet, includes placing a stopper in connection with the outlet, the stopper including a first or air side, a second or fluid side and a passage therethrough from the first side to the second side. The method further includes providing a fluid connector in connection with the stopper. The connector includes a base which includes at least one air conduit and at least one fluid conduit therethrough. The base further includes an extending section. The extending section includes a first abutment member and a second abutment member spaced from the first abutment member. The extending section extends through the passage such that the first abutment member abuts the first side and the second abutment member abuts the second side and seals the passage.

In a number of embodiments, the method further includes pulling the extending section of the base through the passage in the stopper so that the second abutment member abuts the stopper. The first abutment member can, for example, extend radially outward from the extending section of the base and is spaced from the second abutment member so that upon pulling a length of the extending section through the passage, the first abutment member contacts the first side of the stopper and maintains the second abutment member in compressive and sealing abutment with the stopper.

In a further aspect, a method of providing fluid connection to a container, which includes an outlet, includes removably connecting a cap assembly to the outlet. The cap assembly includes an annular cap member connected to a pierceable stopper. The cap member includes an opening to provide access to the pierceable stopper and a connector section to removably connect the cap assembly to the outlet of the container. The method can further include attaching a connector member to the outlet of the container. The connector member includes a cooperating connector section to which the connector section is removably connectible.

In still a further aspect, a method of providing fluid flow from a connector, which includes a fluid line and an air vent line, includes connecting a source of pressurized gas to the air vent line to pressurize fluid with fluid source in fluid connection with the connector.

The present invention, along with the attributes and attendant advantages thereof, will best be appreciated and understood in view of the following detailed description taken in conjunction with the accompanying drawings.

BRIEF DESCRIPTION OF THE DRAWINGS

FIG. 1A illustrates an embodiment of a spike connector including a flexible and penetrable sterility cover, shield or protector packaged with a fluid container.

FIG. 1B illustrates the spike connector of FIG. 1A removed from the package in alignment to pierce a septum of the fluid container.

FIG. 1C illustrates the spiked connector of FIG. 1A in fluid connection with the fluid container.

FIG. 1D illustrates the spiked connector of FIG. 1A in fluid connection with a transfer set to deliver fluid to, for example, a pumping device such as a syringe or continuous pumping device.

FIG. 1E illustrates an enlarged view of the spike connector of FIG. 1A.

FIG. 3A illustrates an embodiment of a spike connector of the present invention including a spike having a fluid line of enlarged cross-sectional area, wherein the spike connector is in a disassembled or exploded state.

FIG. 3B illustrates the spike connector of FIG. 3A in an assembled state.

FIG. 3C illustrates the spike connector of FIG. 3A used in connection with a flexible and penetrable sterility cover, shield or protector.

FIG. 3D illustrates the spike connector of FIG. 3A in alignment to penetrate a fluid container (fluid bag) and after connection with the fluid bag.

FIG. 4A illustrates a container including a standard elastomeric stopper therein and two embodiments of replacement stoppers adjacent to the container.

FIG. 4B illustrates an embodiment of a connector of the present invention including a sealing connector assembly which passes through a passage in an elastomeric stopper.

FIG. 4C illustrates the connector of FIG. 4B in fluid connection with a container.

FIG. 4D illustrates a fluid connector similar to that of FIG. 4A wherein the connector includes an exterior retainer to retain the stopper in sealing engagement with the container.

FIG. 5A illustrates another embodiment of a fluid connector of the present invention in a partially disassembled state.

FIG. 5B illustrates a partially transparent view of the fluid connector of FIG. 5A in an assembled or connected state.

FIG. 5C illustrates a partially transparent view of the fluid connector of FIG. 5A in operative connection with a compressible stopper.

FIG. 9A illustrates a side disassembled or exploded view of an embodiment of a system of the present invention including a combination container cap and stopper wherein an operator can either spike the stopper using a spiked connector or remove the cap to, for example, fill the syringe with a quick fill tube.

FIG. 9B illustrates a side view of the system of FIG. 9A wherein threading of the system has been placed in connection with a standard container.

FIG. 9C illustrates a side view of the system of FIG. 9A wherein the cap and stopper assembly has been placed in operative connection with the threading on the container.

FIG. 9D illustrates a top view of the system of FIG. 9A wherein the cap and stopper assembly is in operative connection with the container and a protective covering has been removed.

DETAILED DESCRIPTION

Figure 1H:
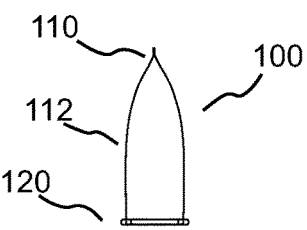
FIG. 1H illustrates another side view of the flexible sterility cover, rotated approximately 90° about its axis from the view of FIG. 1F.

As used herein and in the appended claims, the singular forms "a," "an", and "the" include plural references unless the content clearly dictates otherwise. Thus, for example, reference to "a filter" includes a plurality of such filters and equivalents thereof known to those skilled in the art, and so forth, and reference to "the filter" is a reference to one or more such filters and equivalents thereof known to those skilled in the art, and so forth.

FIGS. 1A through 1H illustrate an embodiment of a sterility cover, protector or shield 100 for use in connection with a fluid connector 200 (or spike connector). Fluid connector 200 includes a piercing spike 210 to pierce a septum or elastomeric stopper 310 of a fluid container or bottle 300 to place a fluid line or channel passing through spike 210 of fluid connector in fluid connection with container 300. Fluid connector 200 also includes a check ball and air filter 220 in fluid connection with an air line or vent line passing through spike 210. As used herein, the term "spike" refers generally to an extending section which tapers over at least a portion thereof to a generally pointed end suitable for piercing.

Fluid connector 200 further includes a swabable valve 230 to, for example, connect to a transfer set 400 as illustrated in FIG. 1D. Suitable swabable valves are, for example, disclosed in U.S. Pat. No. 6,651,956 and are commercially available from Halkey-Roberts Corporation of Saint Petersburg, Fla. External surfaces in the proximity of a valve stem of swabable valve 230 are accessible to be wiped with a sterile swab. Valve 230 can, for example, connect to a first luer-type connector 410 on a first end of a transfer set 400, which can further include flexible tubing 420 and a second luer-type connector 430 on a second end thereof. Second luer-type connector 430 can, for example, be connected to a pressurizing device 500 such as a syringe in operative connection with a powered injector (for example, a STELLANT injector available from Medrad, Inc. of Indianola, Pa.) or a continuous pump as, for example, described in U.S. Pat. Nos. 5,916,197 and 6,197,000 and illustrated in FIG. 1D (not to scale).

Figure 8A:
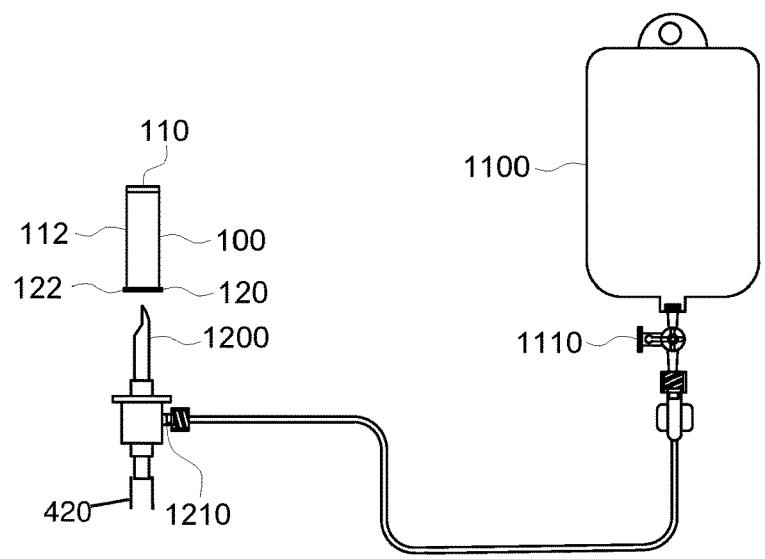
FIG. 8A illustrates an embodiment of a system including a fluid connector and a source of pressurized gas in connection with the air line or vent of the fluid connector.
Figure 8B:
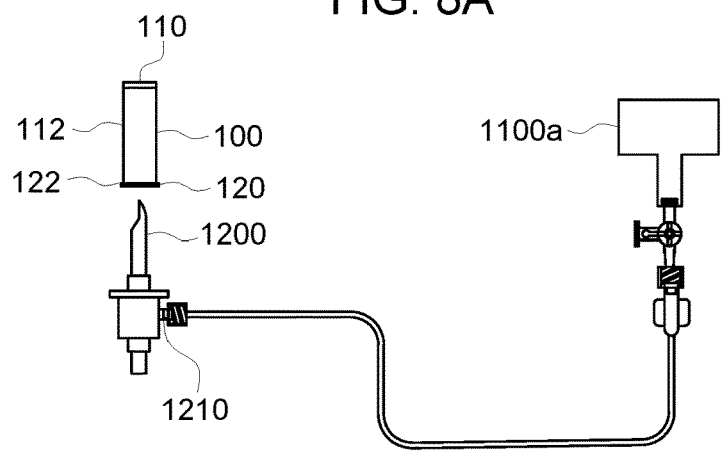
FIG. 8B illustrates an embodiment of a system including a fluid connector and a gas/air compressor in connection with the air line or vent of the fluid connector.
Figure 8C:
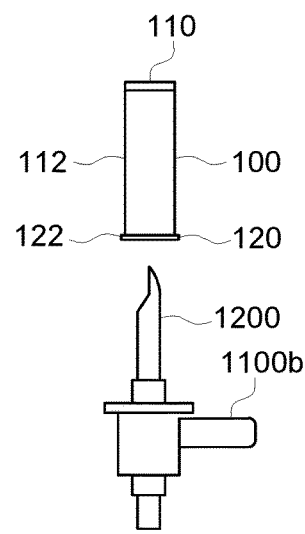
FIG. 8C illustrates an embodiment of a system including a fluid connector and a compressed gas cartridge in connection with the air line or vent of the fluid connector.

In the embodiment illustrated in FIGS. 1A through 1H and 8A-8C, flexible, protective covering or shield 100 is provided over spike 210. Cover 100 includes a first, closed end 110 that is pierceable, tearable or breakable by spike 210. First end 110 can, for example, be formed of a pierceable, tearable or breakable material such as a polymeric/elastomeric material or a paper material. A body or side section 112 can, for example, be formed from a flexible or collapsible material such as a polymeric film or a paper, which is connected to or formed integrally with first end 110. As illustrated in FIG. 1H and FIGS. 8A-8C, in one embodiment, body section was formed to be generally cylindrical and the forward end thereof (that is, the end proximate the tip of spike 210) was closed or sealed (for example, via heat sealing, adhesive etc.) to create closed, first end 110. Cover 100 further includes a second end or base 120. In several embodiments, such as shown in FIGS. 8A-8C, second end 120 included a generally annular elastomeric member 122 that attaches to spike of fluid connector 1200 via compressive pressure applied by the elastomeric member. Cover 100 can, for example, be attached to or placed in connection with spike of fluid connector 1200 in many different manners to retain cover 100 in connection with spike of fluid connector 1200 (for example, via an adhesive).

In the embodiment of FIGS. 1A through 1G, cover 100 is generally in the form of a closed sleeve having a diameter or cross-sectional area only slightly larger than that of spike 210. Forming cover 100 as a relatively close-fitting sleeve assists in ensuring that cover 100 does not interfere with the normal operation of connector 200.

Protective cover 100 can be sterilized and distributed in operative connection with sterilized connector 200 in sterile packaging 600 (see FIG. 1A), which can, for example, also include sterilized container 300. Protective cover 100 assists in maintaining the sterility of spike 210, for example, after removal from package 600 and during piercing of/fluid connection with septum or stopper 310.

As illustrated in FIG. 1B, after connector 200 is removed from packaging 600, spike 210 is aligned with septum 310 and contacted therewith. Application of force to connector 200 in a direction toward container 300 will cause spike 210 to pierce or otherwise open first end 110 of cover 100 and then pierce septum 310. As spike 210 is forced through septum 310 and into container 300, flexible body section 112 folds or collapses into a collapsed state as illustrated in FIGS. 1C and 1D. During the insertion process, however, protective cover 100 maintains the sterility of spike 210. As a further precaution, a sterilizing swab can, for example, be applied to at least second end 120 of protective cover 100 prior to contact with septum 310 if there is concern that protective cover 100 has contacted a non-sterile surface after removal from packaging 600.

Figure 1F:
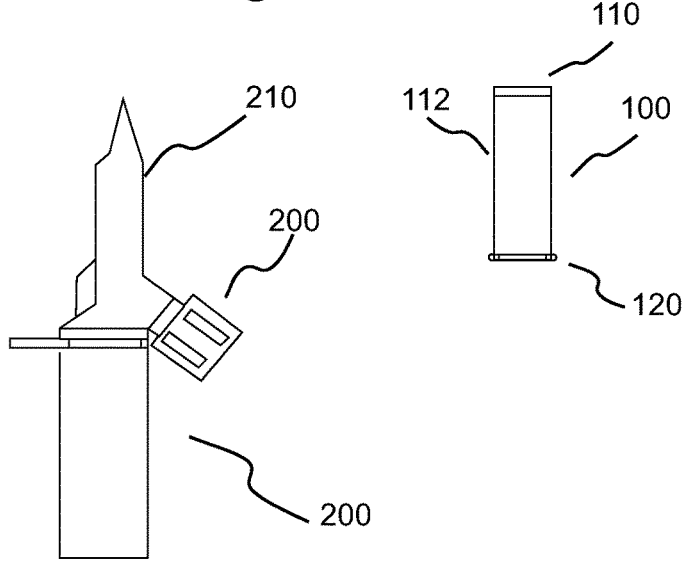
FIG. 1F illustrates a side view of the spiked connector of FIG. 1A with the flexible sterility cover removed from connection therewith.
Figure 1G:
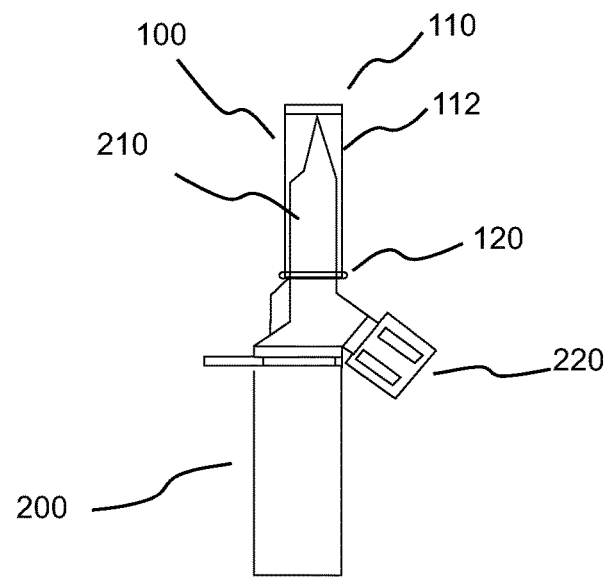
FIG. 1G illustrates another enlarged view of the spiked connector of FIG. 1A.
Figure 2A:
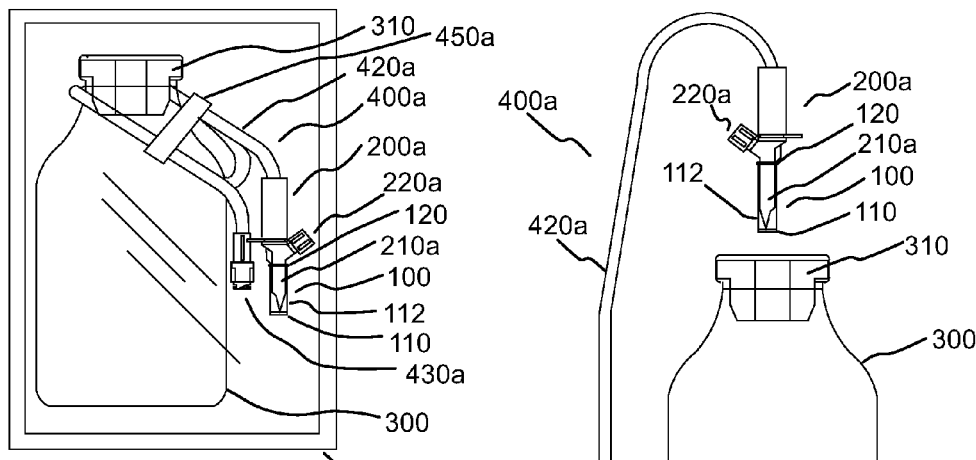
FIG. 2A illustrates an embodiment of a system or kit including a transfer set, which includes a spike connector having a flexible and penetrable sterility shield or protector, packaged with a fluid container.
Figure 2B:
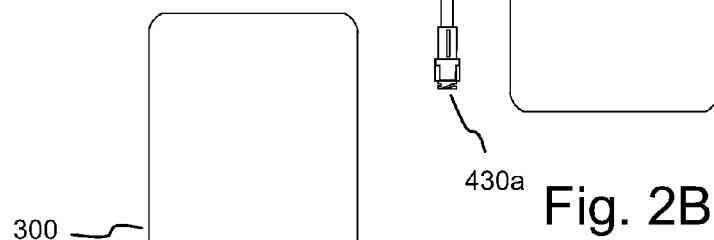
FIG. 2B illustrates the system of FIG. 2A removed from the package with the spiked connector in alignment to pierce a septum of the fluid container.
Figure 2C:
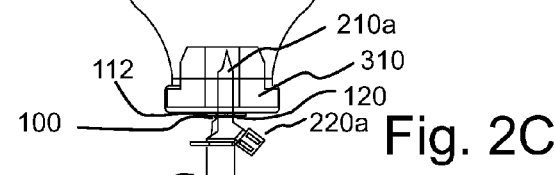
FIG. 2C illustrates the spiked connector and transfer set of FIG. 2A in fluid connection with the container, wherein the container is inverted to, for example, deliver fluid to a pumping device such as a syringe or continuous pumping device.
Figure 2D:
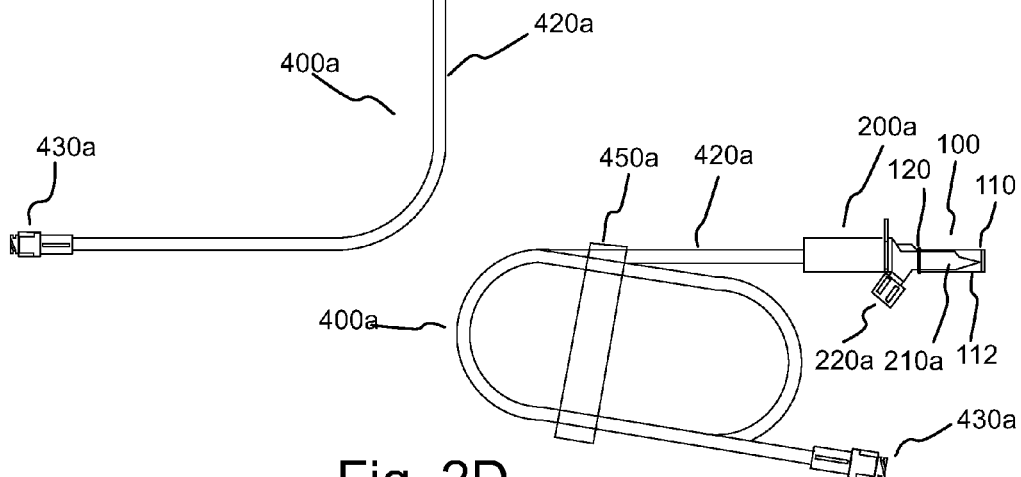
FIG. 2D illustrates an enlarged view of the transfer set of FIG. 2A.
Figure 5D:
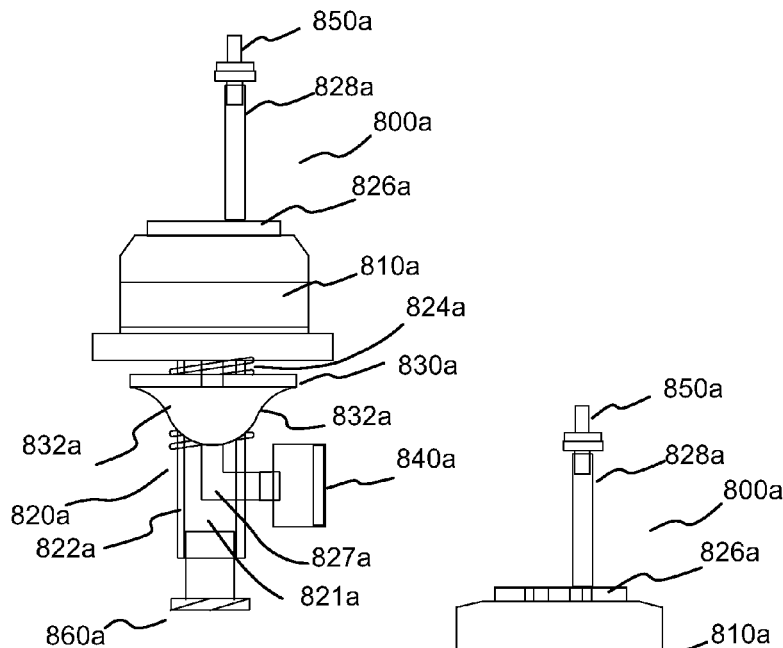
FIG. 5D illustrates another view of the fluid connector of FIG. 5A in operative connection with the compressible stopper.
Figure 5E:
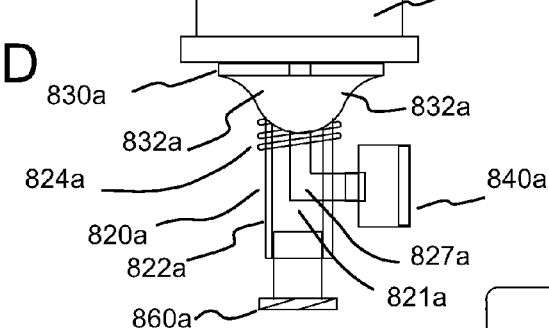
FIG. 5E illustrates operation of the fluid connector of FIG. 5A to form a seal with and compress the compressible stopper.
Figure 5F:
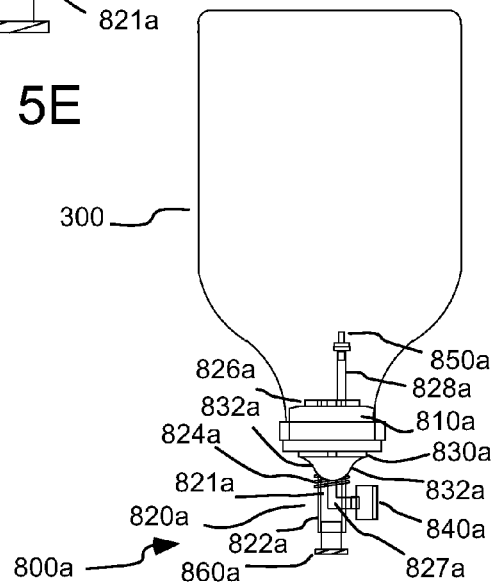
FIG. 5F illustrates the fluid connector of FIG. 5A in operative connection with a fluid container.

FIGS. 2A through 2D illustrate another embodiment of a fluid delivery system including container 300, a transfer set 400a and a fluid connector 200a. In the embodiment illustrated in FIGS. 2A through 2D, fluid connector 200a is permanently connected to or formed as an integral component of transfer set 400a. In other respects, the fluid delivery system of FIGS. 2A through 2D is similar to that of FIGS. 1A through 1G and elements of the fluid delivery system of FIGS. 2A through 2D are numbered similarly to corresponding elements of the fluid delivery system of FIGS. 1A through 1G with the addition of the designation "a" thereto. As illustrated in FIG. 2A, container 300, a transfer set 400a and a fluid connector 200a can be packaged together in sterile packaging 600a. In the illustrated embodiment, a band 450 is placed around coiled tubing 420a of transfer set 400a and tubing 420a is placed around the top of container 300 in packaging 600a.

FIGS. 3A through 3D illustrates another embodiment of a fluid connector 700 including a spike 710. Spike 710 includes at least one fluid flow line, conduit or channel therethrough that has a larger diameter or cross-sectional area larger than found in currently available spiked fluid connectors. In several embodiments, spike 710 was a cannula formed from a relatively stiff material (for example, a metal, a polymeric material or other material) to facilitate a relatively thin wall and a relatively large fluid channel therein. Forming spike or cannula 710 from a metal can, for example, provide for suitable stiffness and a relatively thin wall to allow piercing of a container septum (for example, a septum of a port 310' of a fluid bag 300' as illustrated in FIG. 3D) with large diameter spike 710. In the illustrated embodiment, a connector base 720 is in fluid connection with a male luer-type or luer connector 730 at a first end thereof. Connector base 720 is in fluid connection with spike 710 at a second end thereof. In the illustrated embodiment, a cylindrical or tubular section 740 (for example, a silicon tube section) encompasses spike 710 and acts as a guide in placing connector 700 in operative, fluid connection with port 310' as illustrated in FIG. 3D. As illustrated in FIG. 3C, protective cover 100 can be used in connection with fluid connector 700.

As described in connection with spike 710, a number of fluid connectors of the present invention include at least one fluid flow line, conduit or channel therethrough that has a larger diameter or larger cross-sectional area than found in currently available spiked fluid connectors (for example, greater than 0.008 in$^2$). In several embodiments, the fluid line of the fluid connectors of the present invention has a minimum cross-sectional area of at least 0.010 in$^2$, at least 0.016 in$^2$, at least 0.020 in$^2$, or at least 0.030 in$^2$. The relatively large fluid line or lines can sustain flow rates of, for example, 30 ml/sec or higher using, for example, a heated (to approximately, 98.6° C.) contrast fluid having a viscosity in the range of approximately 10-12 centipoise. For example, one fluid connector of the present invention (that is, connector 1000 of FIGS. 7A through 7K) had a fluid line having a minimum cross-sectional area (the area in the vicinity of the fluid inlet ports) of approximately 0.038 in$^2$. A sustained flow rate of greater than 30 ml/sec with a heated contrast fluid having a viscosity in the range of approximately 10-12 centipoise was achieved. A sustained flow rate of greater than 50 ml/sec with that fluid connector with water (having a viscosity of approximately 1 centipoise) was achieved. These flow rates were achieved in drawing the fluid from a container such as bottle container 300 or bag container 300' under atmospheric pressure using three-valve continuous flow pump 500 (see FIG. 1D) as disclosed in U.S. Pat. Nos. 5,916,197 and 6,197,000, which was operated under power of a motor 510.

FIGS. 4A through 4D illustrate another embodiment of a fluid delivery system for delivery of a fluid from a container 300. In the illustrated embodiment, container 300 includes a stopper 310 in the outlet thereof as described above. A fluid connector 800 includes a replacement stopper 810 including a passage or conduit 812 therethrough. FIG. 4A also illustrates an alternative stopper 810' including a passage 812' the generally conforms to the shape of a second abutment member 826 of fluid connector 800 discussed below. A base 820 of connector 800 can, for example, include a fluid flow line, conduit or channel (not shown) therethrough of relatively large cross-sectional area to accommodate relatively high flow rates. To place connector 800 in fluid connection with container 300, stopper 310 is removed from container 300 and replaced with fluid connector 800, including stopper 810.

In assembling connector 800, an extending section 822 of base 820 is passed through passage 812 in stopper 810 until a first abutment member in the form of a threaded compression sleeve 830 can form a threaded connection with threading 824 on base 820. Connector 800 can then be placed in fluid connection with container 300 via stopper 810 with first abutment member 830 on a first or fluid side of stopper 810 and second abutment member 826 on a second or fluid side of stopper 810.

In that regard, base 820 includes a wedge-shaped, lower or second abutment member 826. The radius of base 820 increases over the length of second abutment member 826. Rotation of threaded first abutment member 830 relative to base 820 draws second abutment member 826 within passage 812, sealing passage 812. The drawing of second abutment member 826 within passage 812 also causes compression of stopper 810 (which can, for example, be formed from a silicone rubber) against the inner diameter of the outlet of container 300, thereby improving the sealed connection therewith and creating a generally leakproof seal.

Compression of stopper 810 by second abutment member 826 assists in retaining stopper 810 in sealing engagement with container 300 when, for example, container is inverted to deliver fluid. In an alternative embodiment illustrated in FIG. 4D, a retainer or retaining cap 870 (including an opening 872 through which an upper portion of fluid connector 800 can pass) forms, for example, a snap fit with container 300 to assist in retaining stopper 810 in sealing engagement with container 300, even when inverted. In the embodiment of FIG. 4D, a second abutment member 830' need only form a sealing engagement with stopper 810 (sealing passage 812) and need not (but may) compress stopper 810.

An air filter 840 is in fluid connection with an air line (not shown) in the vicinity of and air side end of extending section 822. An air check valve 850 is in fluid connection with the air line at an opposite end 828 (that is, the fluid side end) of the air or vent line. Inclusion of check valve 850 in air filter line reduces or eliminates the chances of liquid entering and clogging filter 840, which can result in deterioration of the operation of connector 800. The inclusion of check valve 850 can, for example, be beneficial if reuse of connector 800 is desired.

A connector 860 such as a luer-type connector is placed in fluid connection with the fluid line extending through base 820 at the end of extending section 822. Connector 860 can, for example, be placed in fluid connection with a transfer set such as transfer set 400 described above.

Use of connector 800, including replacement stopper 810, facilitates the incorporation of relatively large fluid conduits within the connector. Such large (inner diameter) fluid conduits enable one to achieve relatively high flow rates as compared to currently available spiked fluid connectors.

FIGS. 5A through 5F illustrate another embodiment of a fluid delivery system for delivery of a fluid from container 300, which is similar in design and operation to the fluid delivery system of FIGS. 4A through 4C. Elements of the fluid delivery system of FIGS. 5A through 5F are numbered similarly to corresponding elements of the fluid delivery system of FIGS. 4A through 4C with the addition of the designation "a" thereto.

Fluid connector 800a includes a replacement stopper 810a including a passage or conduit 812a therethrough. A base 820a of connector 800a can, for example, include a relatively large inner diameter passage, conduit or fluid line 821a therethrough. To place connector 800a in fluid connection with container 300, stopper 310 is removed from container 300 and replaced with fluid connector 800a, including stopper 810a.

In assembling connector 800a, an extending section 822a of base 820a is passed through passage 812a in stopper 810a until a threaded first abutment member 830a (which can include radially extending flanges or fins 832a to facilitate grasping) can form a threaded connection with threading 824a on base 820a. Connector 800a can then be placed in fluid connection with container 300 via stopper 810a.

Base 820a includes a second abutment member including a flange 826a which extends generally perpendicular to the longitudinal axis of base 820a. As, for example, illustrated in FIGS. 5D and 5E, rotation of first abutment member 830a (which abuts a first or air side of stopper 810) relative to base 820a draws second abutment member into sealing contact with stopper 810a, further causing compression of stopper 810a (which can, for example, be formed from a silicone rubber) and forcing stopper 810a against the inner diameter of the outlet of container 300, thereby improving the seal therewith and creating a generally leakproof seal.

An air filter 840a is in fluid connection with an air line 827a formed in base 820a in the vicinity of an end of extending section 822a. An air check valve 850a is in fluid connection with air line 827a at an opposite end 828a of base 820a. As described above, inclusion of check valve 850a in air filter line 827a reduces or eliminates the chances of liquid entering and clogging filter 840a.

A connector 860a such as a luer-type connector or a swabable valve can be placed in fluid connection with fluid line 821a extending through base 820a at the end of extending section 822a. Connector 860a can, for example, be placed in fluid connection with a transfer set such as transfer set 400 described above.

FIGS. 6A through 6D illustrate another embodiment of a fluid delivery system or fluid connector for delivery of a fluid from a container such as container 300. Similar to the fluid delivery systems or connectors of FIGS. 4A through 5F, fluid connector 900 includes a stopper 910 including a passage or conduit 912 therethrough. A base 920 of connector 900 can, for example, include a relatively large inner diameter passage, conduit of fluid line (not shown) therethrough. To place connector 900 in fluid connection with container 300, for example, stopper 310 can be removed from container 300 and replaced with fluid connector 900, including stopper 910. However, connector 900 is preferably used as the original stopper in connection with container 300 upon filling thereof with fluid, obviating the need for replacing stopper 310.

In assembling connector 900, a pull tab section 970, which can extend through passage 912 in stopper 910, is connected to an end of an extending section 922 of base 920. For example, pull tab section 970 can include a connector 972 (for example, a male luer connector) and extending section 922 can include a cooperating connector 960 on an end thereof (for example, a female luer connector). Extending section 922 includes a first abutment member 925. Base 920 further includes a second abutment member or wedge 926 which operates similarly to the second abutment member 826 described in FIGS. 4B and 4C. In general, the radius of base 920 increases over the length of the second abutment member 926 to generally form a wedge.

In deployment or activation of connector 900, one first removes an optional sterile cover 905. The user can then grasp a pull tab 974 of pull tab section 970 and pulls extending section 922 of base 920 through passage 912 in stopper 910. Second abutment member 926 is thereby drawn within passage 912, sealing passage 912 and causing compression of stopper 910 (which can, for example, be formed from a silicone rubber) against the inner diameter of the outlet of container 300, thereby improving the seal therewith and creating a generally leakproof seal. Base 920 is drawn upward (in the orientation of FIGS. 6A through 6C) until first abutment member 925 is drawn through passage 912 and a lower (once again, in the orientation of FIGS. 6A through 6C) surface of first abutment member 925 abuts an upper surface of stopper 910, thereby locking base 920 in the deployed or active position illustrated in FIG. 6A. At this point, pull tab section 970 can be removed and a fluid line such as transfer set 400 can be attached to fluid connector 900 via connector 960.

Figure 6A:
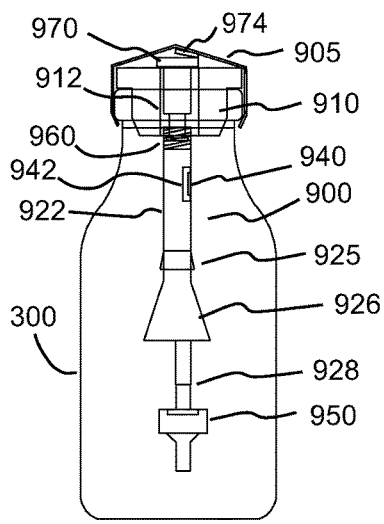
FIG. 6A illustrates an embodiment of a fluid connector of the present invention wherein the fluid connector is positioned within a container in a non-deployed or storage state.
Figure 6B:
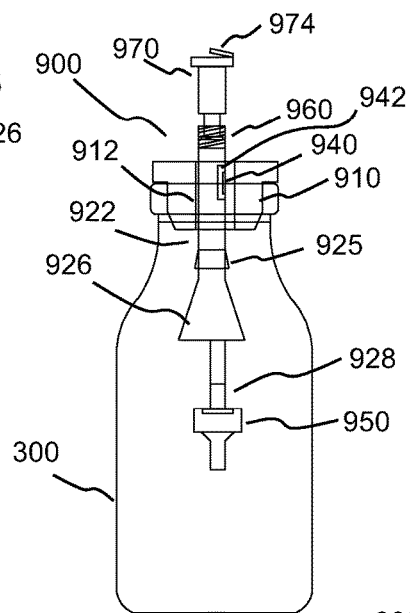
FIG. 6B illustrates initial unsealing and deployment of the fluid connector of FIG. 6A.
Figure 6C:
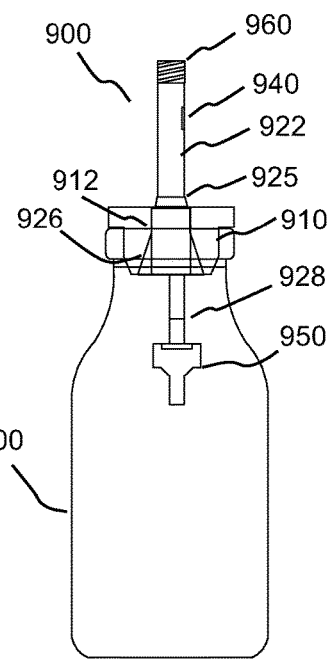
FIG. 6C illustrates full deployment of the fluid connector of FIG. 6A.
Figure 6D:
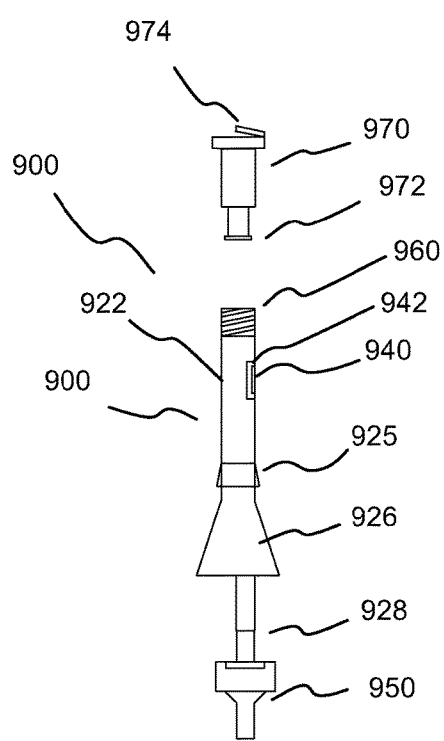
FIG. 6D illustrates an enlarged disassembled or exploded view of the fluid connector of FIG. 6A.

An air filter 940 is in fluid connection with an air line (not shown) formed in base 920 and is positioned on base 920 in the vicinity of an end of extending section 922. An air check valve 950 is in fluid connection with the air line at an opposite end 928 of the air line. As described above, inclusion of check valve 950 in the air filter line reduces or eliminates the chances of liquid entering and clogging filter 940. During storage of fluid connector 900 within container 300, a removable, protective covering 942 can be placed over air filter 940 or an inlet thereto. Protective covering 942 can, for example, be formed from a polymeric film with an adhesive on one side there of to adhere to base 920 and prevents fluid from entering air filter 940 when fluid connector 900 is stored within container 300. When fluid connector 900 is deployed (as illustrated in FIG. 6C), protective covering 942 is removed to allow air to enter container 300 during flow therefrom.

FIGS. 7A through 7K illustrate another embodiment of a fluid connector 1000 including an extending section 1022 in the form of a tapered or pointed spike to pierce stopper 310 of container 300. Extending section or spike 1022 includes a fluid line 1021 (see, for example, FIG. 7F) therethrough of relatively large cross-sectional area as described above to provide increased flow rates as compared to currently available spike connectors. Fluid line 1021 includes at least one inlet 1021a (two in the illustrated embodiment) via which fluid from a container such as container 300 enters the fluid line and an outlet 1060, which can be formed as or can connect to a connector (for example, a luer connector) as described above. Extending section 1022 further includes an air or vent line 1027 (see, for example, FIG. 7F) therethrough including at least one outlet 1027a. Alternatively, a check valve 1050 can be incorporated into filter 1040 or extending section 1022. A check valve 1050, which is incorporated into extending section 1022, is in fluid connection with air line 1027. An air filter 1040 is in fluid connection with an inlet 1027b of air line 1027 (see, for example, FIGS. 7C and 7F).

In the illustrated embodiment, fluid line 1021 was of a generally circular cross-sectional shape. Just downstream (that is, toward outlet 1060) from the centerline of fluid line inlets 1021a, extending section had an outer diameter of approximately 0.327 in. The wall thickness was approximately 0.30 in, resulting in an inner diameter $D_1$ of approximately 0.267 in (see FIGS. 7G and 7H). The cross-sectional area (that is, a minimal cross-sectional area) of fluid line 1021 at that point was calculated to be approximately 0.038 $in^2$. The inner diameter of fluid line increased to a maximum inner diameter $D_2$ of approximately 0.375 in (see FIG. 7G) over the length of extending section 1022, corresponding to a calculated maximum cross-sectional area of approximately 0.063 $in^2$. The wall thickness remained generally constant at approximately 0.030 in. As described above, a sustained flow rate of greater than 30 ml/sec for a heated contrast fluid and a sustained flow rate of greater than 50 ml/sec for water were achieved through fluid connector 1000 in drawing the fluid from a container under atmospheric pressure using three-valve continuous flow pump 500.

Connectors 1000 used in the above-described studies were formed from an epoxy resin in a stereolithography or SLA system. In general, connectors of the present invention can be made from a variety of material including, but not limited to, metals and/or polymeric materials. Suitable polymeric materials for connectors of the present invention include, but are not limited to, acrylonitrile butadiene styrene (ABS) and polyvinyl chloride (PVC).

Extending section 1022 includes a first abutment member 1030 to abut a first or air side of stopper 310 and a second abutment member 1025 spaced from first abutment member 1030 to abut a second of fluid side of a pierceable septum of stopper 310 to retain fluid connector 1000 in fluid connection with stopper 310 and container 300. In that regard, enlargement of extending section 1022 (as compared to currently available fluid connector spikes) results is substantial force exerted by elastomeric stopper 310 upon extending section 1022 tending to push fluid connector out of connection with stopper 310. The entrapment of a portion of stopper 310 between first abutment member 1030 and second abutment member 1025 prevents disengagement. To facilitate full connection of fluid connector 1000 with stopper 310, wherein the pierceable portion of stopper 310 is engages on the first side thereof by first abutment member 1030 and on the second side thereof by second abutment member 1025, fluid connector 1000 includes extending flanges 1032 to facilitate rotation or twisting of fluid connector 1000 during penetration of stopper 310. An outlet 1060 of fluid connector 1000 can include a connector such as luer connector as described above to, for example, attach transfer set 400. A filter (not shown) as described above can also be placed in fluid connection with the air side end of the air line.

FIG. 8A illustrates the use of a source or reservoir 1100 of low pressure (but higher than atmospheric pressure) gas (for example, sterile air) in fluid connection with an air vent 1210 of a fluid connector 1200 to increase the flow rate of fluid through the fluid line of fluid connector 1200 when fluid connector is in fluid connection with a container such as container 300. Source 1100 can, for example, include a refill port 1110.

FIG. 8B illustrates a source of pressurized gas (for example, air) including a compressor 1100a in fluid connection with air vent 1210 of fluid connector 1200 to increase the flow rate of fluid through the fluid line of fluid connector 1200.

FIG. 8C illustrates a source of pressurized gas (for example, air or sterile air) including a cartridge 110b in fluid connection with air vent 1210 (not shown in FIG. 8C) of fluid connector 1200 to increase the flow rate of fluid through the fluid line of fluid connector 1200. Sources of pressurized gas such as described in connection with FIGS. 8A through 8C can be used in connection with virtually any fluid connector including an air vent line to increase fluid flow through the fluid line of the fluid connector.

Figure 7B:
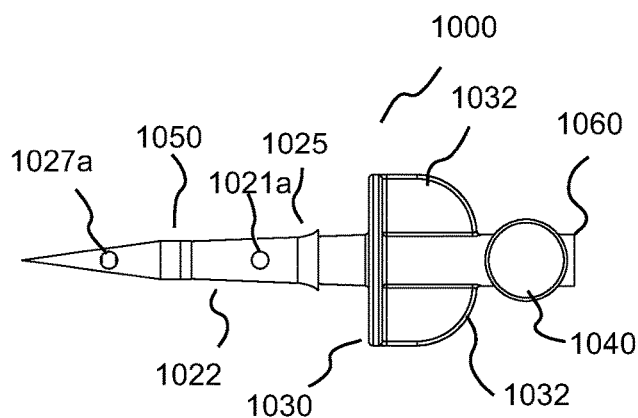
FIG. 7B illustrates a side view of the fluid connector of FIG. 7A.
Figure 7A:
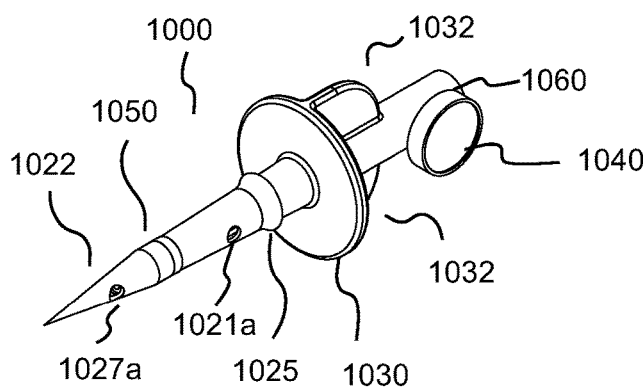
FIG. 7A illustrates a perspective view of an embodiment of a fluid connector of the present invention.
Figure 7C:
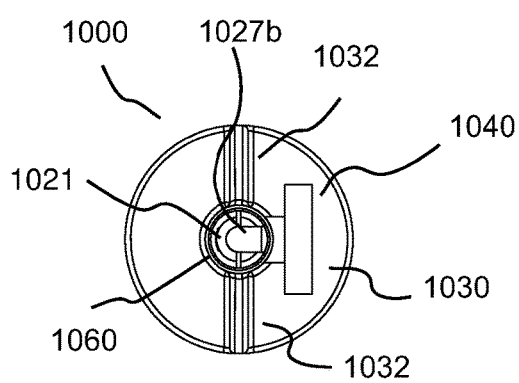
FIG. 7C illustrates a rear or top view of the fluid connector of FIG. 7A.
Figure 7D:
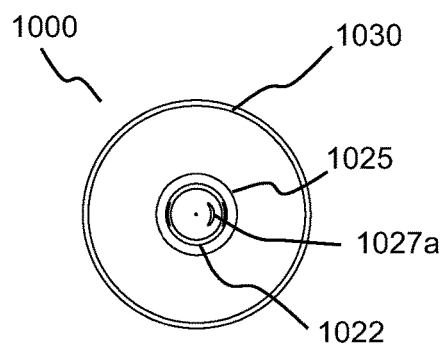
FIG. 7D illustrates a forward or bottom view of the fluid connector of FIG. 7A.
Figure 7F:
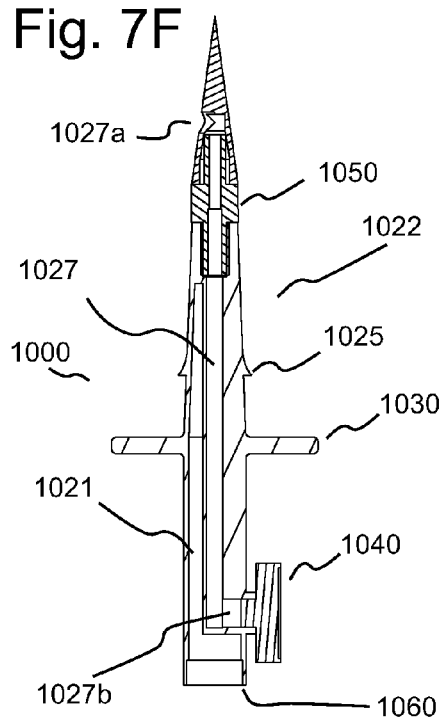
FIG. 7F illustrates a side, cross-sectional view of the fluid connector of FIG. 7A.
Figure 7E:
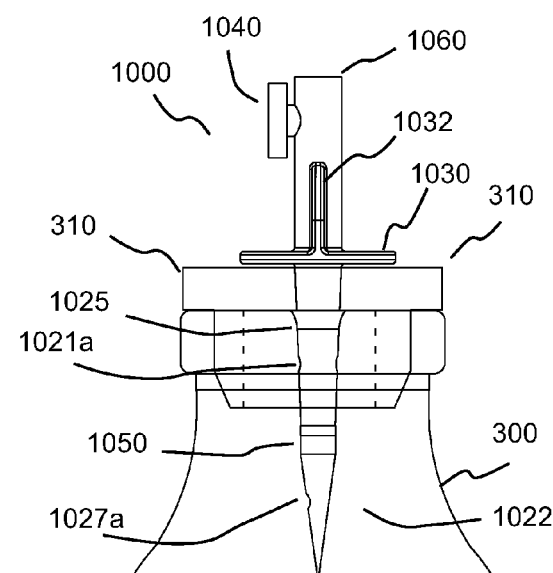
FIG. 7E illustrates the fluid connector of FIG. 7A in fluid connection with a septum of stopper of a container.
Figure 7G:
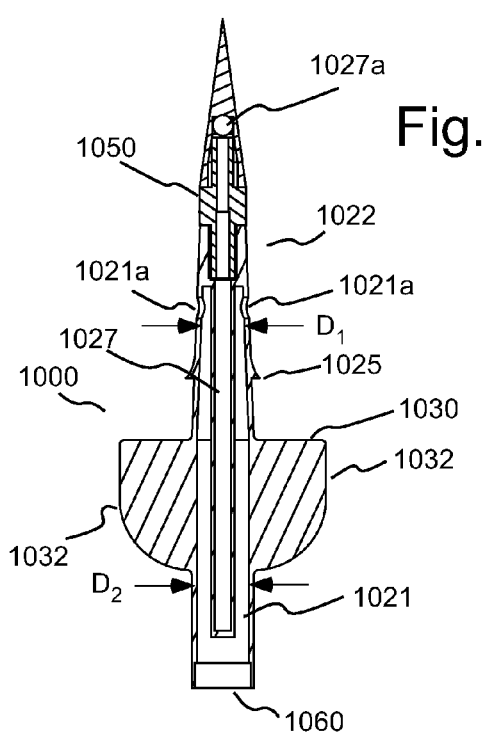
FIG. 7G illustrates another side, cross-sectional view of the fluid connector of FIG. 7A.
Figure 7H:
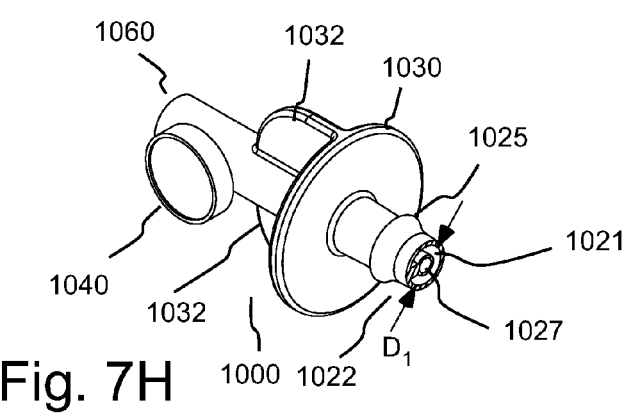
FIG. 7H illustrates a perspective, partially cutaway view of the fluid connector of FIG. 7A.
Figure 7I:
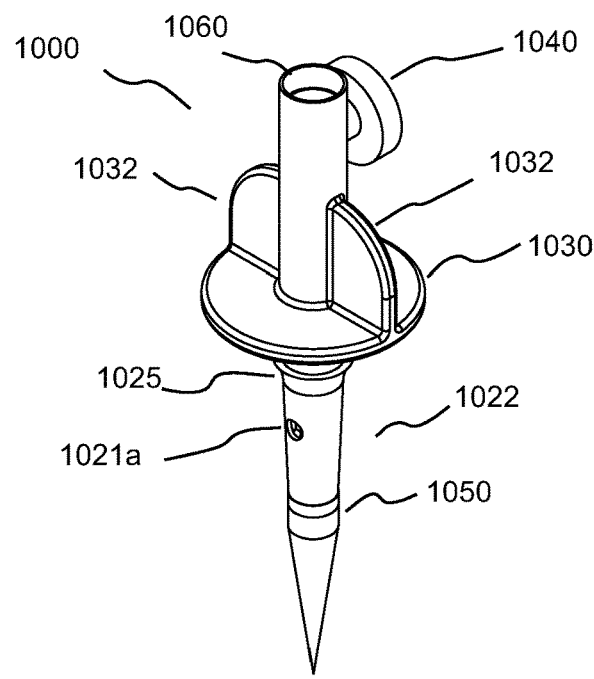
FIG. 7I illustrated another perspective view of the fluid connector of FIG. 7A.
Figure 7J:
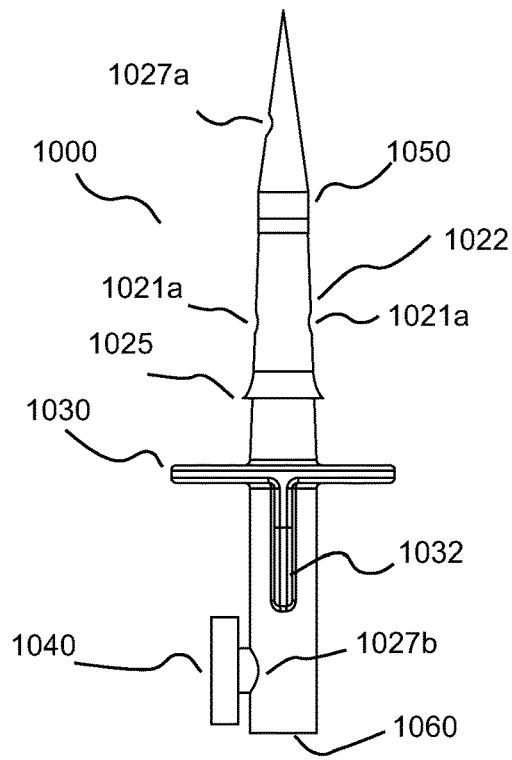
FIG. 7J illustrates another side view of the fluid connector of FIG. 7A.
Figure 7K:
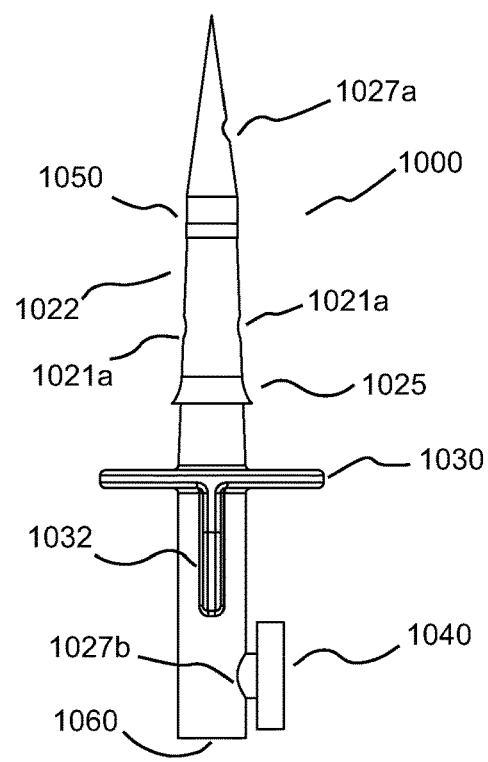
FIG. 7K illustrates another side view of the fluid connector of FIG. 7A.

FIGS. 9A through 9D illustrate a system for converting a container such as bottle 300 to a container that can either be spiked using a spiked fluid connector (as, for example, illustrated in FIGS. 1A through 3C and 7A through 7D) or the cap can be removed to enable access to the fluid within bottle 300 via, for example, a quick fill tube to, for example, fill a syringe. In the illustrated embodiment, system 1300 includes a generally cylindrical or annular cap member 1310 (formed, for example, from a polymeric material) which forms a connection (for example, via a friction fit, snap fit and/or an adhesive or other bond) with a stopper member 1320. System 1300 also includes a generally cylindrical or annular connector member 1330 (formed, for example, from a polymeric material) which includes a connection section such as a threading section that connects to the outlet section of container 300 (for example, via an overforming process or an adhesive or other bonding process) as illustrated in FIG. 7B. An inner wall of cap member 1310 includes cooperating connecting section such as a cooperating threading section so that cap assembly 1340 (including cap member 1310 and attached stopper member 1320) is removably and sealingly attachable to connector member 1330, which is attached to container 300. System 1300 can also include a protective covering 1350 (for example, a polymeric film) to, for example, assist in maintaining sterility and to provide an indication of tampering. A pull tab 1352 can be provided to assist removal of covering 1350. When cap assembly 1340 is attached to container 300, and covering 1350 is removed, an upper surface of stopper member 1320 is accessible via an opening 1312 (see FIG. 9D) in an upper end of cap member 1310. As described above, cap assembly 1340 can be removed from connection with container 300 by twisting cap assembly 1340 to disengage cap member 1310 from connection with connector member 1330.

In many currently available containers for pharmaceuticals (such as contrast media) which include a pierceable stopper, a user can remove a metal tab from the container to remove the pierceable stopper, enabling pouring of fluid from the container or use of a fill tube (to, for example, fill a syringe). However, removal of metal tabs on currently available containers can cause a safety hazard as a result of remaining sharp metal edges. These edges can easily cut or pierce surgical gloves. In the case system 1300, in which stopper 1320 is attached to removable cap 1310, the stopper can be removed without worry of creating sharp metal edges. Further, if removal of cap assembly 1340 is not desirable, a user can spike stopper 1320 in the usual manner.

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A fluid connector for use with a pierceable container port, comprising:
   an extending section comprising a spiked end to pierce a pierceable container port, the extending section comprising at least one air conduit and at least one fluid conduit therethrough, a first abutment member and a second abutment member, the first abutment member being adapted to abut a first or air side of the pierceable container port upon piercing of the pierceable container port, the second abutment member being spaced from the first abutment member and being adapted to abut a second or fluid side of the pierceable container port; and
   a pair of grasping members each having a first side integrally formed with the extending section and a second side integrally formed with the first abutment member, the pair of grasping members positioned opposite one another, each of the grasping members extending radially outward from the extending section and axially away from the first abutment member and the second abutment member to facilitate rotation of the extending section relative to a pierceable container port during piercing thereof.

2. The fluid connector of claim 1, further comprising a check valve in fluid connection with the at least one air conduit.

3. The fluid connector of claim 2, wherein the check valve is positioned within the extending section.

4. The fluid connector of claim 1, wherein the at least one fluid conduit has a cross-sectional area of at least 0.02 in$^2$.

5. The fluid connector of claim 1, wherein the at least one fluid conduit has a cross-sectional area of at least 0.038 in$^2$.

6. The fluid connector of claim 1, wherein the at least one fluid conduit has a cross-sectional area sufficient to provide a sustained flow rate of greater than 30 ml/sec for a heated contrast fluid.

7. The fluid connector of claim 1, wherein the at least one fluid conduit has a cross-sectional area sufficient to provide a sustained flow rate of greater than 50 ml/sec for a water.

8. The fluid connector of claim 1, wherein the pierceable container port comprises a stopper and the first abutment member and the second abutment member entrap a portion of the stopper therebetween to prevent disengagement of the extending section from the pierceable container port.

9. The fluid connector of claim 1, wherein the at least one air conduit further comprises a filter in fluid connection with an air side end of the at least one air conduit.

* * * * *

UNITED STATES PATENT AND TRADEMARK OFFICE
CERTIFICATE OF CORRECTION

PATENT NO. : 10,105,486 B2  
APPLICATION NO. : 15/173962  
DATED : October 23, 2018  
INVENTOR(S) : Trombley, III et al.

Page 1 of 1

It is certified that error appears in the above-identified patent and that said Letters Patent is hereby corrected as shown below:

In the Drawings

In Fig. 1F, Sheet 2 of 13, delete " 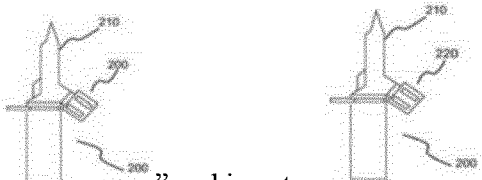 " and insert --  --, therefor.

In Fig. 3A, Sheet 4 of 13, delete " 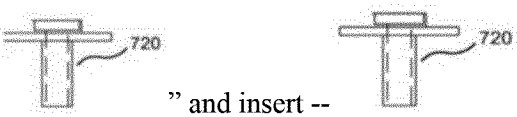 " and insert --  --, therefor.

In Fig. 5C, Sheet 6 of 13, delete "  " and insert -- 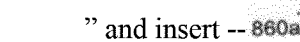 --, therefor.

In the Specification

In Column 13, Line 11, delete "cartridge 110b" and insert -- cartridge 1100b --, therefor.

In the Claims

In Column 14, Line 16, in Claim 1, delete "port, comprising:" and insert -- port, the fluid connector comprising: --, therefor.

Signed and Sealed this  
Fifteenth Day of January, 2019

Andrei Iancu  
*Director of the United States Patent and Trademark Office*